United States Patent [19]

Zick

[11] 4,269,684

[45] May 26, 1981

[54] APPARATUS FOR OXYGEN PARTIAL PRESSURE MEASUREMENT

[75] Inventor: Gregory L. Zick, Kirkland, Wash.

[73] Assignee: Cordis Corporation, Miami, Fla.

[21] Appl. No.: 80,257

[22] Filed: Oct. 1, 1979

[51] Int. Cl.³ ............................................. G01N 27/46
[52] U.S. Cl. ................................. 204/195 R; 73/1 G; 128/635; 204/195 P
[58] Field of Search .............. 204/195 P, 195 R, 1 Y, 204/1 P; 73/1 G; 422/98; 128/635

[56] References Cited

U.S. PATENT DOCUMENTS

| 3,678,375 | 7/1972 | McFarland | 204/195 P |
| 3,794,575 | 2/1974 | Niedrach et al. | 204/195 P |
| 4,120,770 | 10/1978 | Kessler | 204/195 R |

OTHER PUBLICATIONS

Gregory L. Zick, IEEE Trans. On Instrumentation & Measurement, vol. 1M-25, No. 3, pp. 250-253, (1976).

Stanley H. Saulson, Instrumentation & Methods, pp. 29-34.
Albert Huch et al., Hospital Practice, p. 43, Jun. 1976.
Patrick Eberhard et al., "Oxygen Transport Problems In Neonatology", pp. 1097-1101, (1973).
Gregory L. Zick, IEEE Trans. On Biomedical Engineering, vol. BME-23, No. 6, pp. 472-478, (1976).

*Primary Examiner*—G. L. Kaplan
*Attorney, Agent, or Firm*—Kenway & Jenney

[57] ABSTRACT

Disclosed is apparatus and method for continuously compensating for electrode drift during the measurement of the partial pressure of oxygen by the net charge transport technique. The apparatus derives a correction factor from variations in waveforms representing charge returned from an electrochemical cell after successive interrogating voltage pulses. These wave-forms are independent of oxygen partial pressure but dependent on electrode parameters thereby permitting drift to be monitored and oxygen partial pressure measurements to be corrected.

4 Claims, 5 Drawing Figures

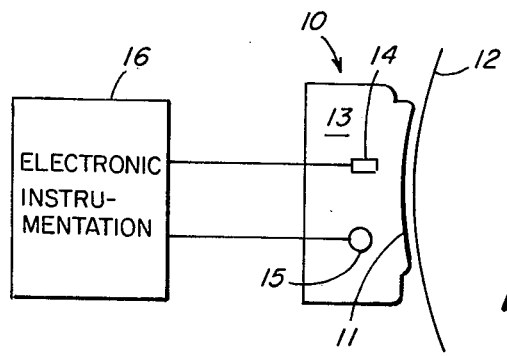
FIG. 1
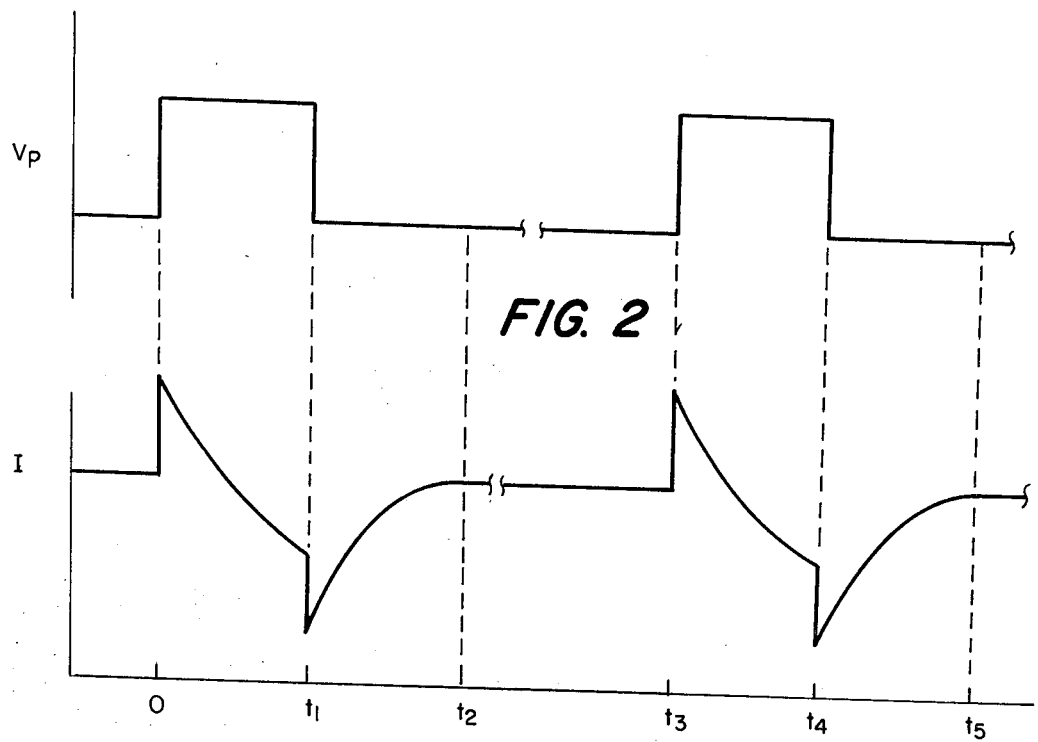
FIG. 2
FIG. 3
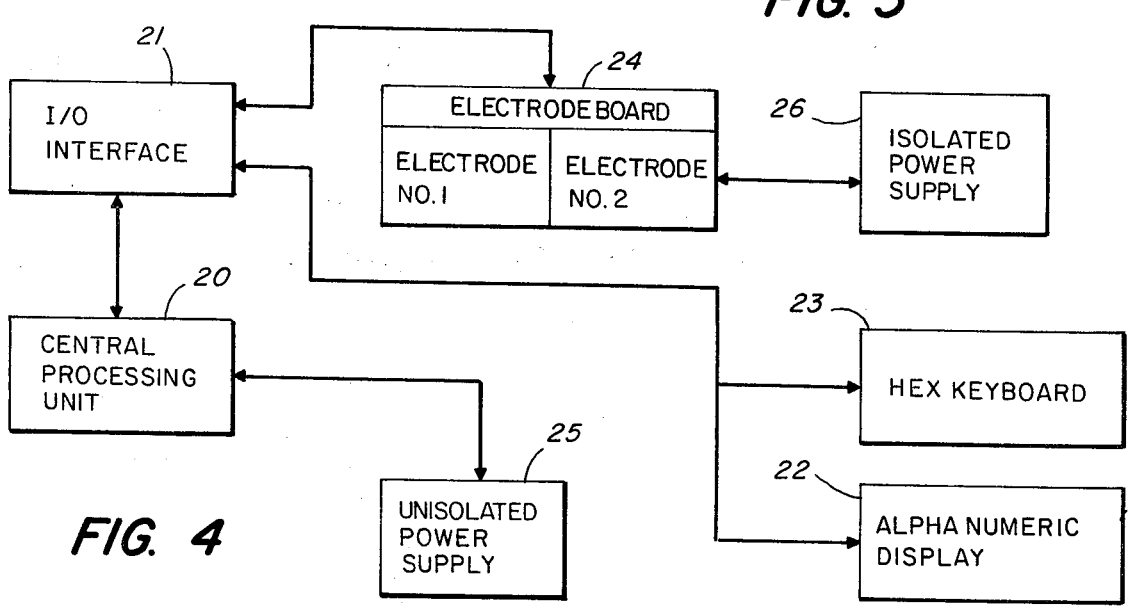
FIG. 4

APPARATUS FOR OXYGEN PARTIAL PRESSURE MEASUREMENT

BACKGROUND OF THE INVENTION

This invention relates to the measurement of the partial pressure of oxygen and more particularly to apparatus and method for continuously compensating for oxygen electrode drift.

Typical oxygen sensors consist of an anode and a cathode immersed in an electrolyte. The electrodes and electrolyte are contained within a membrane which blocks passage of the electrolyte but which allows molecular oxygen to pass through freely. One important oxygen sensor measures the oxygen which perfuses through the skin. In operation, such a transcutaneous sensor is placed against skin, for example, the wrist, which has been heated to cause hyperemia within the underlying capillaries. The increased blood flow elevates the capillary blood oxygen partial pressure to a level approaching that of arterial blood. Thus, the oxygen which perfuses from the capillaries through the heated skin gives an indication of the oxygen partial pressure of arterial blood.

Successive electrical voltage pulses are applied across the electrodes of such oxygen sensors thereby causing current to flow via three mechanisms. The first mechanism is the ion-electron transfer within the electrolyte. The second is the current flow associated with charging the so-called double layer at the electrode-electrolyte interface. This double layer may thus be thought of as acting as an electrical capacitor. The third mechanism, the one of interest, is current flow associated with the reduction of molecular oxygen. Thus, only part of total charge transferred to the cell during a voltage pulse is a function of the concentration of oxygen within the electrolyte. After the pulse, charge is returned from the cell, the amount of charge so returned being nearly independent of the oxygen partial pressure. The charge returned from the cell arises primarily from discharge of the double layer. Because the charge returned from the cell is nearly independent of oxygen concentration whereas the charge delivered to the cell is so dependent, the difference is proportional to the partial pressure of oxygen ($po_2$) in solution. The use of this difference in inferring $po_2$ is known as the net charge transfer technique. This difference between the charge delivered to and returned from the cell, however, is still subject to the very serious problem of oxygen electrode drift. Changes in the amount of charge returned from the cell from pulse to pulse thus indicate changes in the electrodes themselves which give rise to drift, since the charge so returned is nearly independent of the quantity to be measured—the partial pressure of oxygen in solution.

The drift or "aging" associated with oxygen electrodes has several origins. One cause of drift is the precipitation of insoluble salts on the electrode surfaces which reduce their effective area. Another cause is the attraction of large protein molecules to the cathode. Although considerable effort has been devoted to minimizing drift, its elimination has not been achieved. Heretofore, such electrode drift has necessitated frequent instrument calibration and recalibration, greatly reducing the utility of measuring the partial pressure of oxygen using an electrochemical cell.

It is an object of the present invention, therefore, to provide apparatus and method for continuously compensating for electrode drift in the net charge transport technique for determining oxygen partial pressure.

SUMMARY OF THE INVENTION

The apparatus disclosed herein compensates for electrode drift in the net charge transport technique for determining the partial pressure of oxygen in solution. This technique comprises providing an electrochemical cell having an anode and a cathode immersed in an electrolyte and disposed for contact with oxygen. Successive voltage pulses are applied across the cell causing current to flow. For each pulse, the difference between the amount of charge delivered to the cell during the pulse and the amount of charge returned from the cell after the pulse is determined. This charge difference indicates an uncorrected value of the oxygen partial pressure.

The apparatus disclosed herein compensates for electrode drift by multiplying the charge difference by a function of a correction factor derived from the variation between a first transient waveform representing the charge returned from the cell as a function of time after a first pulse and a second transient waveform representing the charge returned from the cell as a function of time after a succeeding pulse.

In a preferred embodiment, the correction factor is the percent change equal to the quotient of the amount of charge returned from the cell after a first pulse minus the amount of charge returned from the cell after a succeeding pulse divided by the amount of charge returned from the cell after the first pulse. The function of the correction factor which multiplies the charge difference to give the corrected value of oxygen partial pressure is one plus the correction factor. In this embodiment, the amount of charge delivered to the cell during one of the pulses is determined by integrating the current waveform for the duration of the pulse and the amount of charge returned from the cell after the pulse is determined by integrating the current waveform from the end of the pulse for a time equal to that of the first integration.

BRIEF DESCRIPTION OF THE DRAWING

The invention disclosed herein may be better understood with reference to the following drawing of which:

FIG. 1 is a conceptual representation of a transcutaneous oxygen sensor;

FIG. 2 is a graphical representation of a polarizing pulse produced by the electronic instrumentation of FIG. 1;

FIG. 3 is a graphical representation of the waveform of current through the electrochemical cell;

FIG. 4 is a block diagram of the oxygen sensing system according to the present invention.

DESCRIPTION OF THE PREFERRED EMBODIMENT

Figure 5:
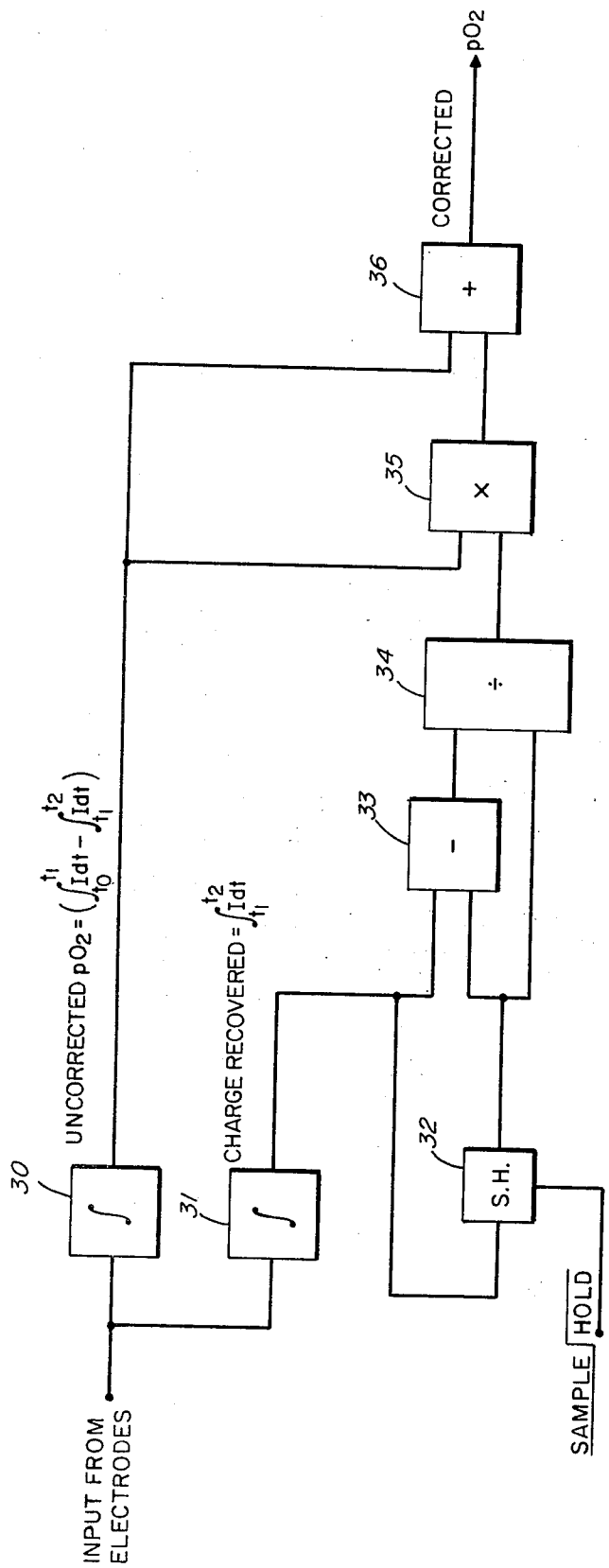
FIG. 5 is a block diagram representing an analog implementation of the present invention.

FIG. 1 depicts the concept of detecting the partial pressure of oxygen transcutaneously. Oxygen sensor 10 is disposed so that membrane 11 is in contact with skin 12. The membrane 11 allows oxygen which has perfused through the skin 12 to enter the sensor chamber 13. A suitable membrane is hydroxypropyl methacrylate. Within the chamber 13 are an anode 14 and a cathode 15 immersed in an electrolyte such as a buffered potassium chloride solution. A suitable cathode is made of gold and a suitable anode is made of a silver-silver chloride composition. It is thus seen that the oxygen sensor 10 is an electrochemical cell. Also included in typical sensors (but not shown here) are a heater and a thermistor for measuring temperature. The heater heats the skin to aid oxygen perfusion. A suitable temperature is approximately 43° C.

Still referring to FIG. 1, the sensor 10 is under the control of an electronic instrumentation package 16. The instrumentation package 16 has essentially three functions relating specifically to the sensing of the partial pressure of molecular oxygen. The first function is to control the temperature of the sensor to a constant value by a heating resistor-thermistor combination. The second function is to apply across the anode 14 and cathode 15 square wave polarizing voltage pulses Vp as represented in FIG. 2. The third function is to monitor and operate upon the waveforms representing the current flow through the cell 10 both during and after the polarizing pulse to produce a corrected value of the oxygen partial pressure. FIG. 3 shows representative current flow waveforms in response to the polarizing pulses Vp of FIG. 2.

Now specifically referring to FIGS. 2 and 3, two representative voltage pulses Vp are shown having non-zero values only between times 0 and $t_1$ and $t_3$ and $t_4$. When one such pulse is applied across an electrochemical cell disposed for contact with molecular oxygen in solution, a charging current I flows through the circuit representing the charge being delivered to the cell. At time $t_1$ when the pulse Vp has become zero, the cell returns charge to the external circuit giving rise to the discharge current waveform shown between $t_1$ and $t_2$. The charge delivered to the cell by the pulse Vp is, therefore, given by $$\int_0^{t_1} I \, dt;$$

the charge returned from the cell after Vp becomes zero is given by $$\int_{t_1}^{t_2} I \, dt,$$

where $t_2 = 2t_1$.

The net charge, which is proportional to the partial pressure of oxygen in solution, $po_2$, is thus $$po_2 \propto \int_0^{t_1} I \, dt - \int_{t_1}^{t_2} I \, dt.$$

As discussed hereinbefore, this measured value is subject to error due to electrode drift resulting, for example, from electrode contamination which reduces its effective area. This drift can be detected by comparing the discharge waveforms (that is, the waveforms produced by charge being returned from the cell) produced by successive pulses. As pointed out above, the discharge waveforms are substantially independent of the $po_2$ level; in the absence of drift, the discharge waveform from $t_1$ to $t_2$ would be virtually identical to the discharge waveform from $t_4$ to $t_5$ even if the $po_2$ level had changed in the time between the two pulses. If there is variation in the discharge waveforms between $t_1$ and $t_2$ and $t_4$ and $t_5$, then there has been electrode drift. A correction factor derived from the variation in the discharge waveforms is employed to modify the measured value of $po_2$. A convenient variation between discharge waveforms for deriving a correction factor is the percent change in the amount of charge returned by the cell for successive pulses. That is, a preferred correction factor C may be expressed as $$C = \frac{\int_{t_1}^{t_2} I \, dt - \int_{t_4}^{t_5} I \, dt}{\int_{t_1}^{t_2} I \, dt}$$

With this correction factor, the corrected value of $po_2$ at the time of the current pulse becomes $po_2$ corrected $$\propto \left[ \int_0^{t_1} I \, dt - \int_{t_1}^{t_2} I \, dt \right] [1 + C]$$

FIG. 4 is a block diagram of the overall electronic system according to the present invention which implements the correction techniques discussed above in conjunction with FIGS. 2 and 3.

The control electronics comprises five major modules and two separate power units. A microcomputer, Texas Instruments 9900, includes a central processing unit 20 and an input-output (I/O) interface 21 of conventional design. The central processing unit 20 is a Texas Instruments 100/M board. Alpha numeric display 22 is a self-scan display having a maximum capability of 64 characters (16 characters by 4 lines). Input to the system is accomplished by means of a hex keyboard 23 having a 16 key input pad.

An electrode board 24 carries the analog circuitry for interfacing with the oxygen sensing electrodes. In this case two sensing electrodes can be accomodated. A conventional unisolated power supply 25 is used to power all electronics except for the electrode board 24. The electrode board 24 is powered by a UL approved isolated power supply 26 which has optical isolation on all digital lines to insure patient isolation. The overall electronics system of FIG. 4 has been designed to exceed the requirements of published human patient safety standards currently in practice. The electrode board 24 of FIG. 4 applies the square wave polarizing voltage pulses across the anode and cathode of the oxygen sensor or sensors and monitors the waveforms representing the current flow through the circuit. This is done under the control of the central processing unit 20.

Specifically, the microcomputer comprising the central processing unit 20 stores the overall program for operation of the oxygen measuring system. Several conventional subroutines implement the electrode drift correction procedure. With each polarizing pulse, a SAMPLE routine samples both the polarizing and depolarizing or discharge current waveforms and puts one hundred digitized values into BUFFER. An integration subroutine next calculates from the data stored in BUFFER the areas under the charging or polarizing waveform and under the depolarizing or discharging waveform. These areas represent the net charge transferred to and returned from the electrochemical cell in response to a polarizing pulse. The difference in these two areas is proportional to the uncorrected value of the partial pressure of oxygen. This measured value of $p_{O_2}$ along with the area under the discharging waveform corresponding to the present pulse next enters the correction subroutine. Already stored in this subroutine is the discharging waveform area from an earlier pulse which serves as a reference. The correction algorithm does two things. First, if the area under the discharging waveform for the present pulse differs from the corresponding area for the reference pulse by 10% or more, this fact is displayed to the operator by display 22. If the difference is less than 10%, this percentage change forms the preferred correction factor since any change in discharging waveform area results from electrode drift because the charge returned from the cell is nearly independent of oxygen partial pressure. The uncorrected value of oxygen partial pressure is then multiplied by this correction factor plus one to give the corrected measured value of the partial pressure of oxygen. Although the variation between the amount of charge returned by the cell for successive pulses gives rise to the preferred correction factor, it is to be understood that other indicators of waveform variation are contemplated to be within the scope of this invention.

Although it is preferred that the computation of the corrected value of oxygen partial pressure be performed digitally as described above, the invention disclosed herein may also be practiced using conventional analog techniques.

FIG. 5 shows one such analog implementation. The signal from the oxygen electrode is first integrated by an integrator 30 to produce the uncorrected value of the oxygen partial pressure:

$$p_{O_2} = \int_{t_0}^{t_1} I\,dt - \int_{t_1}^{t_2} I\,dt,$$

where a voltage polarizing pulse is applied across the electrode during the interval from $t_0$ to $t_1$. A second integrator 31 integrates the signal from the electrodes only for the period after the pulse, $t_1$ to $t_2$, when charge is being returned to the external circuit. This value is held in sample and hold element 32. For the next polarizing pulse, the integrator 31 produces the charge returned to the external circuit for that next pulse. These two values representing the amount of charge returned to the external circuit after successive voltage pulses are subtracted in a subtractor 33. This difference is then divided by the first value stored in the element 32 by a dividing element 34. The output from the dividing element 34 is the correction factor C as defined hereinbefore. The output from the dividing element 34 multiplies the output from the integrator 30 in a multiplier 35. The output from the multiplier 35 is then added to the output of the integrator 10 by an adder 36 to give the corrected value for the oxygen partial pressure.

It is thus seen that the invention disclosed herein provides novel apparatus for continuously compensating for electrode drift in the net charge transport technique for determining the partial pressure of oxygen.

What is claimed is:

1. Apparatus for the measurement of the partial pressure oxygen level comprising:
    (1) an electrochemical cell having an anode and a cathode immersed in a electrolyte, said cell disposed for contact with oxygen;
    (2) means for applying successive voltage pulses across said cell;
    (3) means for determining for each of said pulses the difference between the amount of charge delivered to said cell during one of said pulses and the amount of charge returned from said cell after said one of said pulses, said difference indicating an uncorrected value of said oxygen partial pressure; and
    (4) means for multiplying said difference by a function of a correction factor derived from variation between a first transient waveform representing the charge returned from said cell as a function of time after a first of said pulses and a second transient waveform representing the charge returned from said cell as a function of time after a succeeding one of said pulses.

2. The apparatus of claim 1 wherein said correction factor comprises the percent change equal to the quotient of the amount of charge returned from said cell after a first of said pulses minus the amount of charge returned from said cell after a succeeding one of said pulses divided by the amount of charge returned from said cell after said first pulse.

3. The apparatus of claim 2 wherein said function of said correction factor comprises one plus said correction factor.

4. The apparatus of claim 1 wherein said amount of charge delivered to said cell during one of said pulses is determined by integrating with respect to time the charging current waveform for a time equal to the duration of said pulse, and wherein said amount of charge returned from said cell after said one of said pulses is determined by integrating with respect to time the discharging current waveform for a time equal to the duration of said pulse.

* * * * *